United States Patent
Nguyen et al.

(10) Patent No.: US 7,182,731 B2
(45) Date of Patent: Feb. 27, 2007

(54) SUPPORT ARM FOR CARDIAC SURGERY

(75) Inventors: Hieu Cong Nguyen, Denver, CO (US); John Thomas Matthew Wright, Denver, CO (US); David William Skinkle, Denver, CO (US)

(73) Assignee: Genesee Biomedical, Inc., Denver, CO (US)

( * ) Notice: Subject to any disclaimer, the term of this patent is extended or adjusted under 35 U.S.C. 154(b) by 337 days.

(21) Appl. No.: 10/351,456

(22) Filed: Jan. 23, 2003

(65) Prior Publication Data

US 2003/0158542 A1 Aug. 21, 2003

Related U.S. Application Data

(60) Provisional application No. 60/351,986, filed on Jan. 23, 2002.

(51) Int. Cl.
*A61B 1/32* (2006.01)
(52) U.S. Cl. .......................................... 600/229; 600/37
(58) Field of Classification Search .................. 600/37, 600/201, 210, 235, 204, 214, 227–234; 74/502.3, 74/502.4, 502.6; 248/160, 288.31, 279.1, 248/276.1, 288.51, 231.71; 403/143, 56, 403/90; 285/184; 137/583; 269/22, 24, 269/51, 75, 97; 128/879, 898
See application file for complete search history.

(56) References Cited

U.S. PATENT DOCUMENTS

| 3,240,516 A | * | 3/1966 | Barish et al. ................. 403/54 |
|---|---|---|---|
| 3,638,973 A | * | 2/1972 | Poletti ........................ 285/184 |
| 3,858,578 A | * | 1/1975 | Milo ........................... 600/229 |
| 5,513,827 A | * | 5/1996 | Michelson ............... 248/279.1 |
| 5,662,300 A | * | 9/1997 | Michelson ............... 248/279.1 |
| 5,782,746 A |   | 7/1998 | Wright |
| 5,836,311 A |   | 11/1998 | Borst et al. |
| 6,013,027 A | * | 1/2000 | Khan et al. ................. 600/201 |
| 6,019,722 A | * | 2/2000 | Spence et al. ............. 600/210 |
| 6,213,941 B1 |   | 4/2001 | Benetti et al. |
| 6,254,532 B1 | * | 7/2001 | Paolitto et al. ............. 600/201 |
| 6,338,738 B1 | * | 1/2002 | Bellotti et al. ............. 606/232 |
| 6,375,611 B1 | * | 4/2002 | Voss et al. .................. 600/210 |
| 6,464,629 B1 |   | 10/2002 | Boone et al. |
| 6,491,273 B2 | * | 12/2002 | King et al. .............. 248/276.1 |
| 6,506,149 B2 | * | 1/2003 | Peng et al. ................... 600/37 |
| 6,581,889 B2 | * | 6/2003 | Carpenter et al. .......... 248/160 |
| 6,606,921 B2 | * | 8/2003 | Noetzold ................... 74/502.3 |
| 6,688,564 B2 | * | 2/2004 | Salvermoser et al. ....... 248/160 |
| 6,701,930 B2 |   | 3/2004 | Benetti et al. |

(Continued)

OTHER PUBLICATIONS

Akins et al. (1984) American Heart Journal 107:304-308.

(Continued)

*Primary Examiner*—Samuel G. Gilbert
(74) *Attorney, Agent, or Firm*—Swanson & Bratschun LLC

(57) ABSTRACT

A support arm assembly for assisting in the performance of cardiac surgery has an articulated arm movable axially of a support base and rotatable relative to the support base. A distal end of the articulated arm receives a contact member and the contact member is moveable relative to the distal end. A surgeon may configure the support arm assembly to contact a desired portion of a heart and fix the articulated arm, its axial position, its rotated position and the orientation of the contact member with a single control.

12 Claims, 15 Drawing Sheets

U.S. PATENT DOCUMENTS 6,705,988 B2 * 3/2004 Spence et al. .............. 600/201
6,730,020 B2 * 5/2004 Peng et al. ................. 600/201

OTHER PUBLICATIONS

Ankeney (1975) Annals of Thoracic Surgery 19:108-109.
Benetti (1985) J. Cardiovascular Surgery 26:217-221.
Benetti et al. (1991) Chest 100:312-316.
Buffolo & Gerola (1997) Intl Journal of Cardiology 62(Suppl)1:589-593.
Buffolo et al. (1996) Annals of Thoracic Surgery 61:63-66.
Fanning et al. (1997) Annals of Thoracic Surgery 55(2):486-489.
Pfister et al. (1992) Annals of Thoracic Surgery 54:10851092.
Trapp & Bisarya (1975) Annals of Thoracic Surgery 19:1-9.

* cited by examiner

SUPPORT ARM FOR CARDIAC SURGERY

RELATED APPLICATIONS

This application claims priority from U.S. Provisional Patent Application Ser. No. 60/351,986, filed Jan. 23, 2002, entitled "Support Arm for Cardiac Surgery."

TECHNICAL FIELD

The present invention relates generally to surgical tools including surgical tools for cardiac surgery, and more specifically to surgical tools used in conjunction with Coronary Artery Bypass surgery, both the on-pump and the off-pump variety.

BACKGROUND ART

Off-Pump Coronary Artery Bypass (OPCAB) has evolved since about 1990, following the pioneering work done in North America by Ankeney in the period 1970–75, Akins et al. 1979, and Fanning et al. 1979–1992 in the U.S, and by Trapp & Bisarya in the early 1970's in Canada. In South America other pioneering was done by Benetti (1978–85) in Argentina and Buffolo (1981–85) in Brazil. Generally the anastomotic site was immobilized with stay sutures, such as the technique described by Trapp & Bisarya, who encircled the anastomotic area with sutures placed deep in the myocardium to incorporate enough muscle to suspend the heart yet prevent damage to the coronary artery. Later in the U.S. Phister (1985–90) and Gundry in 1990 (among others) performed OPCAB surgery but both had an assistant with a hand held instrument press on the surface of the heart near the anastomotic site to aid in epicardial immobilization.

In the mid 1990's various epicardial stabilizing instrument that could be attached to sternal retractors were evolved. For example U.S. Pat. No. 5,836,311 described a vacuum epicardial stabilizer, U.S. Pat. No. 5,782,746 described an adhesive coated and vacuum epicardial stabilizer, and U.S. Pat. No. 6,213,941 described a mechanical foot that pressed on the myocardium to stabilize the anastomotic site.

During the period of about five or six year following the mid 1990's OPCAB was increasingly used. Some surgeons reported that a great majority of their patients received OPCAB surgery. Initially, one driving force that brought this operative change included the potential to reduce the size of the surgical incision in the patient's chest; a second was the potential of reducing post-operative complications due to embolism or micro-embolism associated with an extracorporeal circulation and the use of the aortic cross-clamp. Perceived advantages were the potential of reducing patient post-operative pain; and the potential to shorten hospital and recovery time and hence reduce overall costs of the treatment procedure. Initially the procedure was called MIDCAB (Minimally Invasive Direct vision Coronary Artery Bypass) surgery (sometimes called "keyhole" surgery). It soon became apparent to many cardiac surgeons that a minimal incision (usually a thoracic as opposed to a sternal incision) was both surgically inadequate, and it resulted in increased post-operative pain as compared with a midline sternotomy. Hence, this procedure fell out of favor after a couple of years.

Some results of OPCAB procedures demonstrated that post-operative embolic complications were reduced, while others did not. Generally, the incidence of postoperative embolic complications did not fall as dramatically as had been expected. However with OPCAB surgery blood loss, and the volume of blood perfused during and following surgery were shown to have been significantly reduced as compared to on-pump bypass surgery. In some studies overall hospital stay and hence treatment cost did fall, although in other studies this was not found to be the case. Operating time generally increased for OPCAB procedures, and this with the high cost of disposable epicardial stabilizers largely offset the cost savings of not using a cardiopulmonary machine with its disposable blood handling circuit components.

To more easily and accurately and speedily anastomose a bypass graft on a coronary artery the immediate surface of the beating heart surrounding the anastomotic site must be rendered relatively akinetic. Stabilization of this local area may be achieved by placing a stabilizing foot (attached to the distal end of a surgical arm) on the surface of the heart to lie on either side of the anastomotic site. The proximal arm is firmly attached to a sternal retractor, thus theoretically fixing and immobilizing the stabilization foot. However, in practice prior instrument have drawbacks that this invention overcomes. For example, most disposable instruments either have a rigid (straight or curved) metal arm, or a fully articulated plastic arm. While the rigid metal arms are fairly stiff, they are not suitable for accessing the proximal obtuse marginal branches of the circumflex coronary arteries on posterior part of the epicardium or the distal circumflex arteries. By contrast, many disposable arms have plastic articulated members. Because Young's Modulus of plastic is low compared to that of stainless steel, flexure of the plastic arm by forces applied by the beating heart to the stabilizing foot causes said arm to flex significantly. Clearly, high rigidity is necessary to minimize movement under load at the anastomotic site as the heart beats. A second important consideration concerns the force that can be applied to the distal portion of the arm before one or more of the nestling articulating joints slip. Obviously the longer the arm, the greater the force moment that causes arm flexure or slippage. If all parts of the heart are to be stabilized an arm of sufficient reach and versatility is required, thus low flexure and slippage under load is advantageous. Moreover, it is highly desirable to provide to the surgeon with multiple types, configurations and sizes of stabilizing, so that the surgeon can select the optimum for individual anatomies.

The majority of the devices currently marketed for myocardial stabilization are only available as single patient use combined arm and feet, the arm and the foot being disposable. The currently marketed devices have some functional shortcomings, and do not offer a full "tool kit" to allow the surgeon to select a device configuration best suited to all surfaces of the heart. In addition, current devices do not provide sufficient adjustability to reach the entire surface of the heart. Furthermore, current devices lack the rigidity necessary to provide a stable support for remote portions of the heart. Finally, existing devices can be cumbersome to use and difficult to secure in a select orientation. The present invention is intended to overcome one or more of the problems discussed above.

SUMMARY OF THE INVENTION

A first aspect of the present invention is a support assembly arm for assisting in the performance of cardiac surgery. The support arm assembly includes an articulated support arm made of a plurality of links having a socket housing at a distal end. A contact member for bearing on the surface of the heart has a ball connected thereto and the ball is received in the socket housing to enable the contact member to assume a select orientation relative to the support arm. A cable extends between the socket housing and a proximal end of the support arm. The cable is operatively associated with the links of the articulated support arm and the socket housing so that when the cable is tensioned it compresses the links to fix a select configuration of the support arm and compresses the socket housing against the ball to fix a select orientation of the contact member relative to the support arm. An apparatus for tensioning the cable is operatively associated with the cable and a clutch is operatively associated with the tensioning apparatus for preventing application of greater than a select tensile force to the cable.

The tensioning apparatus preferably consists of a first end of the cable being fixedly attached to the socket housing and a hole in each link receiving the cable. A knob having a threaded receptacle is attached to a proximal end of the cable and is rotatable about a longitudinal axis of the support arm relative to the plurality of links. A threaded member is received in the threaded receptacle and fixed against rotation relative to the links. A second end of the cable is operatively associate with the threaded member, whereby as the knob is rotated in a first direction the threaded member is advanced within the receptacle to tension the cable and as the knob is rotated in a second direction the threaded member is withdrawn from the receptacle to slacken the cable. The clutch preferably includes at least one radial driver ramp which is fixed against rotation relative to the knob within the knob housing. An Acme nut is received within the knob housing to define the threaded receptacle. The Acme nut has an abutting end having a radial ramp nesting with the radial driver ramp. A spring compresses the radial driver ramp against the Acme nut with the radial driver ramp and the radial nut ramp nested. The radial driver ramp and the radial nut ramp will disengage if a tensile force on the cable exceeds a select amount as the knob is rotated in the first direction.

The first aspect of the support arm assembly may further include a base including a clamp for fixed attachment to a support. An axial clamp extends from the base and axially receives the articulated support arm. The clamp has a locked position preventing axial movement of the support arm relative to the clamp and an unlocked position enabling axial movement of the support arm relative to the clamp. An actuator is associate with the cable for actuating the clamp to the locked position as the cable is tensioned. The base may further include a pivotal connection between the base and the axial clamp enabling rotation of the axial clamp relative to the base and an actuator operatively associated with the cable for fixing the pivotal connection with the clamp in a select rotated position relative to the base as the cable is tensioned.

A second aspect of the present invention is a support arm assembly for assisting in the performance of cardiac surgery having a base including a clamp for fixed attachment to a support. An articulated support arm has a contact member for bearing on the surface of the heart operatively associated with its distal end. An axial clamp extends from the base and axially receives the articulated support arm. The axial clamp has a locked position preventing axial movement of the support arm relative to the axial clamp and an unlocked position enabling axial movement of the support arm relative to the axial clamp, whereby the effective length of the distal end of the support arm relative to the base can be varied. The articulated support may further include a ball and socket connection between the contact member and a distal end of the articulated support arm to enable the contact member to assume a select orientation relative to the articulated support arm. A fixing apparatus is provided operatively associated with the articulated support arm, the axial clamp and the ball and socket connection for fixing the support arm in the select configuration, for fixing the clamp in the locked position and for fixing the ball and socket connection with a select orientation relative to the articulated support arm by actuation of a single control. The support arm assembly may further include a pivotal connection between the base and the axial clamp, enabling rotation of the axial clamp relative to the base and the fixing apparatus then further includes a structure operatively associated with the pivotal connection for fixing the axial clamp in a select rotated position relative to the base by actuation of the single control.

The fixing apparatus preferably includes a cable extending between the ball and socket connection and a proximal end of the articulated arm, with the cable being operatively associated with the articulated support arm, the clamp and the ball and socket connection so that as the cable is tensioned the support arm is fixed in the select configuration, the axial clamp is fixed in the locked position and the ball and socket connection is fixed with a select orientation relative to the support arm. The single control preferably consists of a knob rotatably attached to the proximal end of the support arm, with the cable being operatively associated with the knob and the knob being configured so that as it is rotated in a first direction any tension in the cable is increased and as the knob is rotated in a second direction any tension in the cable is decreased.

Yet another aspect of the present invention is a method for performing a surgical procedure on a heart of a patient. The method includes making an incision in the patient's chest, inserting a retractor into the incision and securing the retractor in an open position to provide access to the heart. An articulated arm having a proximal and a distal end is provided. The articulated arm is attached to the retractor so that the articulated arm is movable axially relative to the retractor and the articulated arm is configured as desired to bring the contact member into contact with a desired portion of the heart. The articulated arm is fixed axially of the retractor and the configuration of the support arm is fixed to exert and maintain a stabilizing force on the desired portion of the heart while performing the surgical procedure. Preferably, fixing of the articulated arm axially of the retractor and fixing the configuration of the support arm is performed by actuation of a single control operatively associated with the proximal end of the articulated arm. Preferably, releasably attaching the interchangeable contact member further includes releasably attaching the interchangeable contact member in a manner allowing for movement of the contact member relative to the distal end of the articulated arm and the interchangeable contact member is oriented relative to the distal end of the articulated arm as desired. The orientation of the interchangeable contact member is then fixed relative to a distal end of the articulated arm. Preferably, the articulated arm is attached to the retractor in a manner allowing the articulated arm to rotate about an axis substantially vertical to the patient's chest and the articulated arm is rotated as desired and the rotational position is fixed in a desired position relative to the retractor.

The method may further include providing a friction fit between the contact member and the distal end of the articulated arm for retaining the contact member connected to the distal end of the articulated arm followed by fixing the contact member to the distal end of the articulated arm in a select orientation.

The surgical procedure may be a coronary artery bypass graft procedure and the desired portion of the heart may be any anastomotic site and the stabilizing force preferably provides surgical exposure to the anastomotic site. Alternatively, the surgical procedure may be a surgical procedure on a cardiac valve and the desired portion of the heart is any portion of the heart improving the surgical exposure to an atrium, aorta or pulmonary artery when the surgical procedure is performed. The support arm may also be used in other surgical procedures using the steps described in the methods above.

The present invention is directed toward an improved platform or support arm from which to base coronary artery surgery, including beating heart stabilization. The invention is intended to provide the surgeon with a versatile, configurable, rigid base to which task specific accessories may be attached. Designed to be reusable, the present invention also offers a lower cost opportunity per procedure.

The present invention incorporates a majority of reusable components, with only certain heart contact component used in coronary artery surgery being disposable. This arrangement combines disposable product economy with high quality and highly effective reusable devices, leading to significant cost reduction per procedure for the hospital. Multiple choice disposable heart contact members allows the surgeon to choose the optimum attachment to suit the procedure and anatomy. Furthermore, the extensive adjustability of the device, including the ability to vary the length of the articulated arm, vary the orientation of the contact member, rotate the contact member axially of the articulated arm axis, and rotate the articulated arm about the base, allows the surgeon access to the entire heart, including the entire external surface of the heart. A desired configuration of all the adjustable elements can then be fixed securely with a single control element, namely the knob at the proximal end of the articulated support arm. A clutch mechanism in the knob prevents over stressing of the components. The stainless steel construction of the device along with the roughened and hardened link interfaces, provides exceptional rigidity and a solid support for any portion of the heart.

The instrument has utility in coronary artery bypass surgery carried out using cardio-pulmonary bypass. In such procedures the support arm for cardiac surgery, with a suitable stabilizing foot, may be used to retract the stationary heart to produce satisfactory surgical exposure of the anastomotic site without the necessity for a surgical assistant who otherwise be required to hold the heart in position, whether using hand held retractors or holding the heart directly. The elimination of this assistant has several advantages to the surgeon and hospital. For example, the surgeon has more freedom in scheduling the time of the operation, which otherwise, depends on the availability of an assistant. A second advantage is that the cost of assistant fee is saved, as well as various sundry hospital costs such as reduced laundry and disposable garment costs.

In addition, the instrument has utility in cardiac valve surgery. In such procedures the support arm for cardiac surgery with a suitable retractor foot, may be used with a simple sternal retractor, to retract the aorta or left and right atrium to produce satisfactory surgical exposure of the cardiac valve without the necessity for an surgical assistant who otherwise be required to expose the valve use using hand held retractors. In such circumstances the use of this support arm for cardiac surgery has the potential for reducing operating room staff and otherwise saving costs.

DETAILED DESCRIPTION OF THE PREFERRED EMBODIMENT

A support arm assembly 100 is comprised of a clamp base 200 an articulated arm 300 and a locking mechanism assembly and torque limiting mechanism 400.

Figure 2:
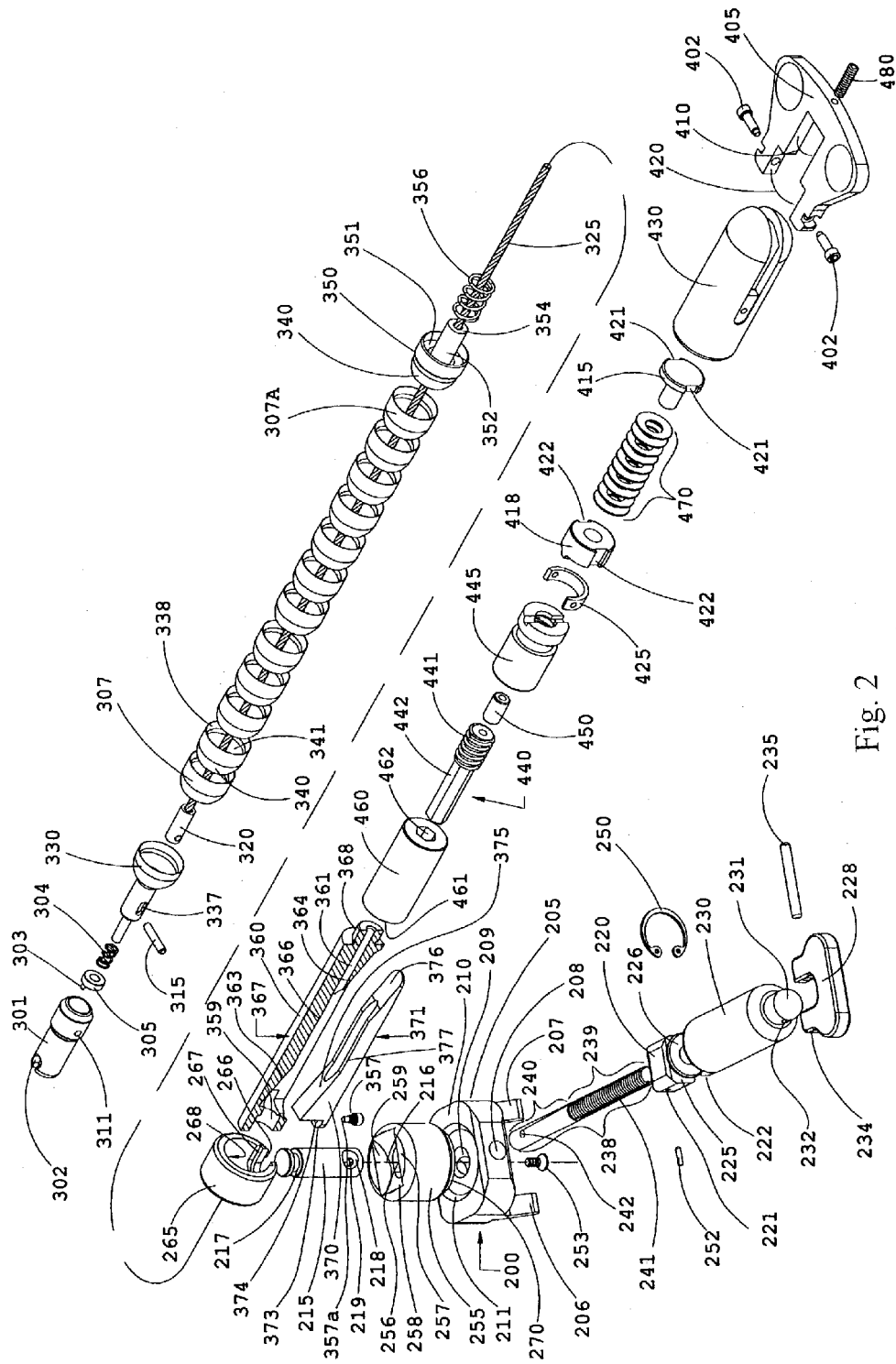
FIG. 2 is an exploded view of the support arm of FIG. 1.
Figure 9:
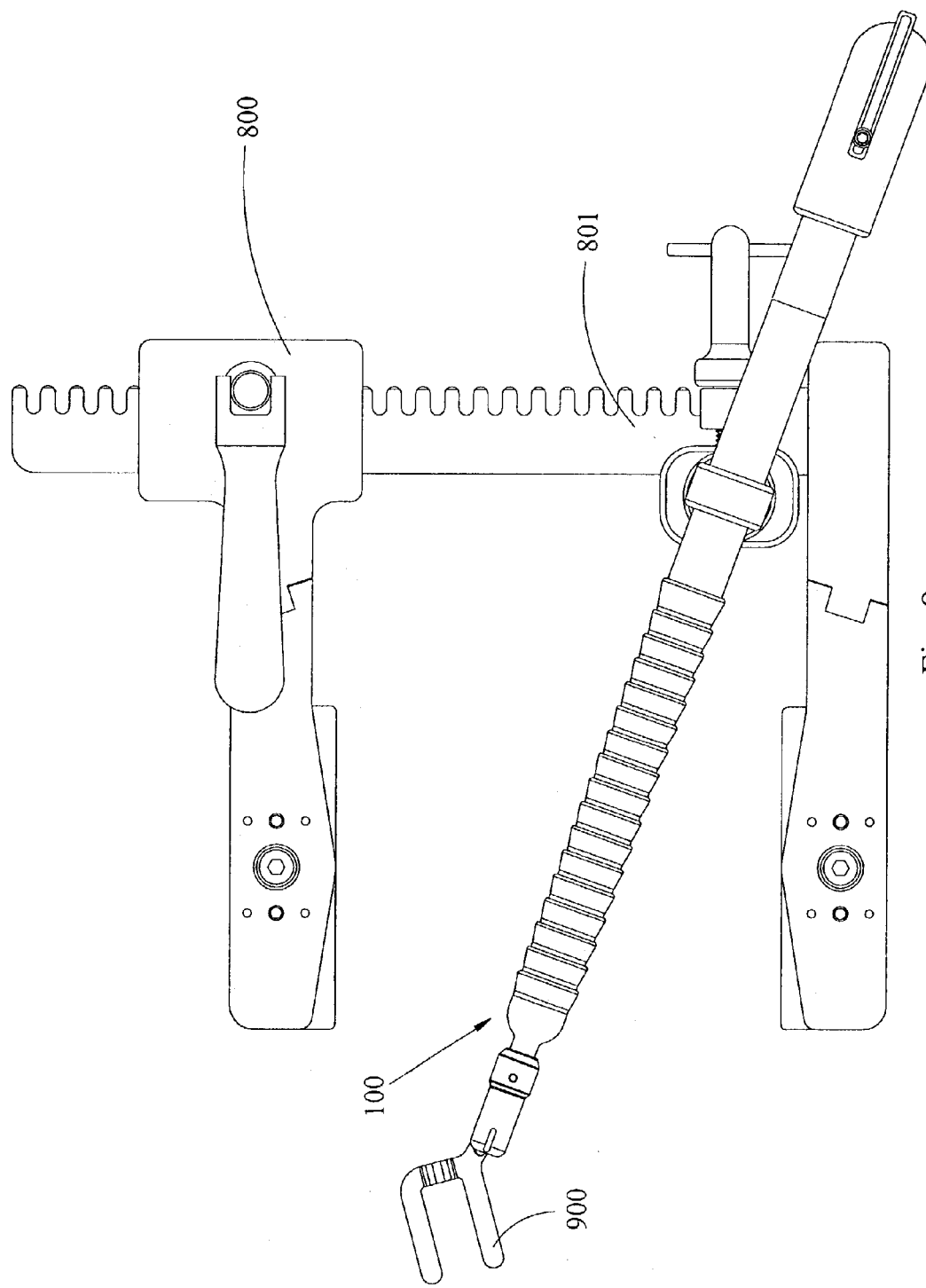
FIG. 9 is a plan view of the support arm according to the present invention mounted on the rack of a sternal retractor, with an epicardial stabilizer attached by the ball receiver. The arm is shown rotated about the clamp base.

Referring to FIG. 2, the clamp 200 base provides a mechanism for attachment by clamping onto the arms or rack of common or specialized sternal retractors (as illustrated in FIG. 9). The clamp base 200 includes a foundation 205 having a pair of spaced grip fingers 206 207, a transverse cylindrical recess 208 at right angles to fingers, not shown, and a vertical central through hole 209. The upper face 210 has tapered recess 211. Opposing clamp base foundation 205 is clamp hook 220 having a grip finger 222 which cooperates with fingers 206, 207 for gripping onto the retractor features. The clamp base 200 also includes a pivot 215 defining a pivotal axis 216 for the articulating arm to be radially positioned relative to clamp base 200. In the present embodiment, the pivot axis is oriented vertically relative to the clamp base foundation 205 and the chest of a patient on whom a procedure is performed and it may be referred to herein as a vertical axis, but this is not intended to limit potential orientations. The pivot 215 has an annular head groove 217 at its upper end, a transverse through hole 218 near its lower end and a concentric countersunk axial hole 219 from its lower face to intersect transverse hole 218. Clamp hook grip body 220 has a small side hole 221 in one side near a proximal face, and an annular groove 225 near a distal flange 226.

Figure 3:
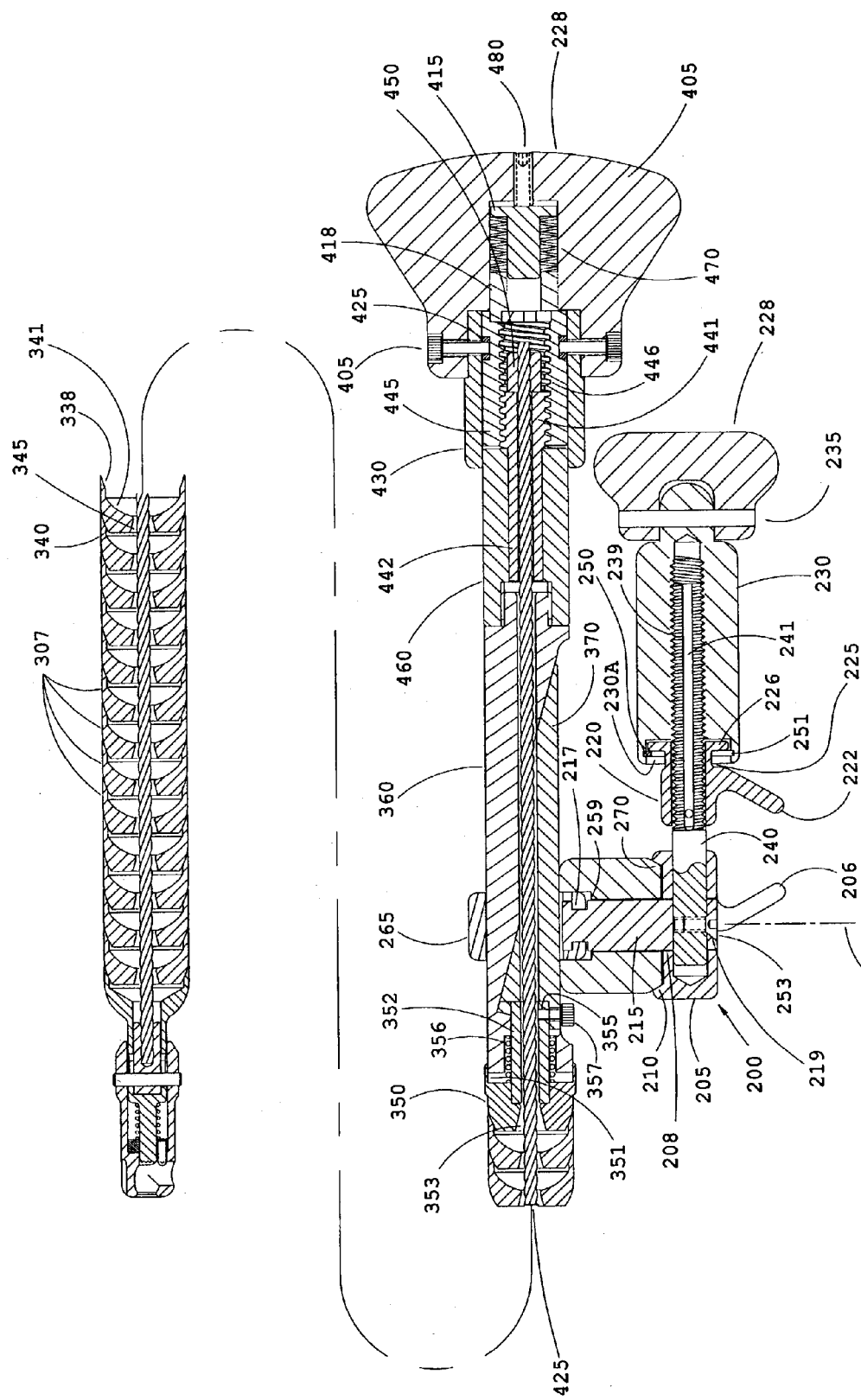
FIG. 3 is a cross-sectional side view of the support arm of FIG. 1.

The clamp base 200 includes has a knob 228 and an internally threaded body 230 having a snout 231 at its distal end with a cross hole 232. Knob 228 has cross holes 234 and is joined to threaded body 228 by a pin 235. The pin 235 is free to rotate in hole 232 but is held in an interference fit in holes 234. Thus knob is free to partially pivot about the axis of pin 235, which is securely retained in knob 228. A clamp shaft 238 has a threaded portion 239, an unthreaded portion 240, an axially extending slot 241 in the threaded portion 239 and a threaded hole 242 offset 90° from the slot 241 near a free end of the unthreaded portion 240. The threaded body 230 threadably receives the threaded portion 239 of the shaft 238. The clamp hook 220 also slidengly axially receives the threaded portion 239 of the shaft 238. The flange 226 of the clamp hook 220 is received in an aperture 230A in the distal end of internally threaded body 230 and secured therein by C clamp 250 received in an annular groove 251 in the aperture 230A of the threaded body, as shown in FIG. 3. Pin 252 received in slot 241 and a corresponding hole 221 in the clamp hook 220 prevents the clamp hook 220 from rotating relative to clamp shaft 238, but allows it to move axially. The pivot 215 is retained in clamp base foundation 205 by the plain proximal portion 240 of shaft 238 which is received in the transverse hole 218. The shaft 238 is in turn retained in position by screw 253 received in hole 219 of pivot 215 which and threadably received in the threaded hole 242, preventing axial or rotational movement of shaft 238 relative to the clamp base. Pivot 215 is concentrically received by a slide cradle 255 having a cylindrical concentric bore 256, a partial elongated semi-circular recess 258 at one end with sides 259 to slideably retain slide loop 265 without undue clearance. It is important that the semi-circular recess 258 be elongated and sufficiently deep to provide clearance for a lower quadrant of slide loop 265. Slide loop 265 has slot 266 in its lower quadrant. The slot has a flat uppermost recess 267 with vertical sides. The width of the slot is such that it will slide onto groove 217 at the upper end of pivot 215. Slide loop 265 has an upper, inner quadrant designated 268. Slide cradle 255 has a male taper 270 on its lower end that mates with female taper 211 on clamp base 205 to provide a self-releasing but high torsional friction interface.

In conjunction with pivot 215, slide loop 265 serves as an axial locking component, and prevents rotation of articulated arm 300 about the pivot axis 216 when the articulated arm 300 is fixed, as described below. The articulated arm 300 provides the versatility and flexibility to be translated and configured into proper configuration for optimal positioning, and then locked into configuration by the turn of a knob. The act of locking the arm also fixes the axial and radial position of the arm and the position of the installed end-accessory. The arm includes a socket housing or receiver 301 that accepts the attachment features of the attachable devices. The present embodiment contemplates this attachment feature to be a ball analogous in form to the ball of a common trailer hitch.

The articulated arm 300 further includes a section of nested articulating links 307, a rigid tubular section comprising a ramp body 360, a machined ramp 370 and an internal hexagonal spacer 460. The ramp body 360 and the machined ramp 370 interface with the clamp base 200, and has a torque-limiting knob system 400 for tightening.

Figure 1:
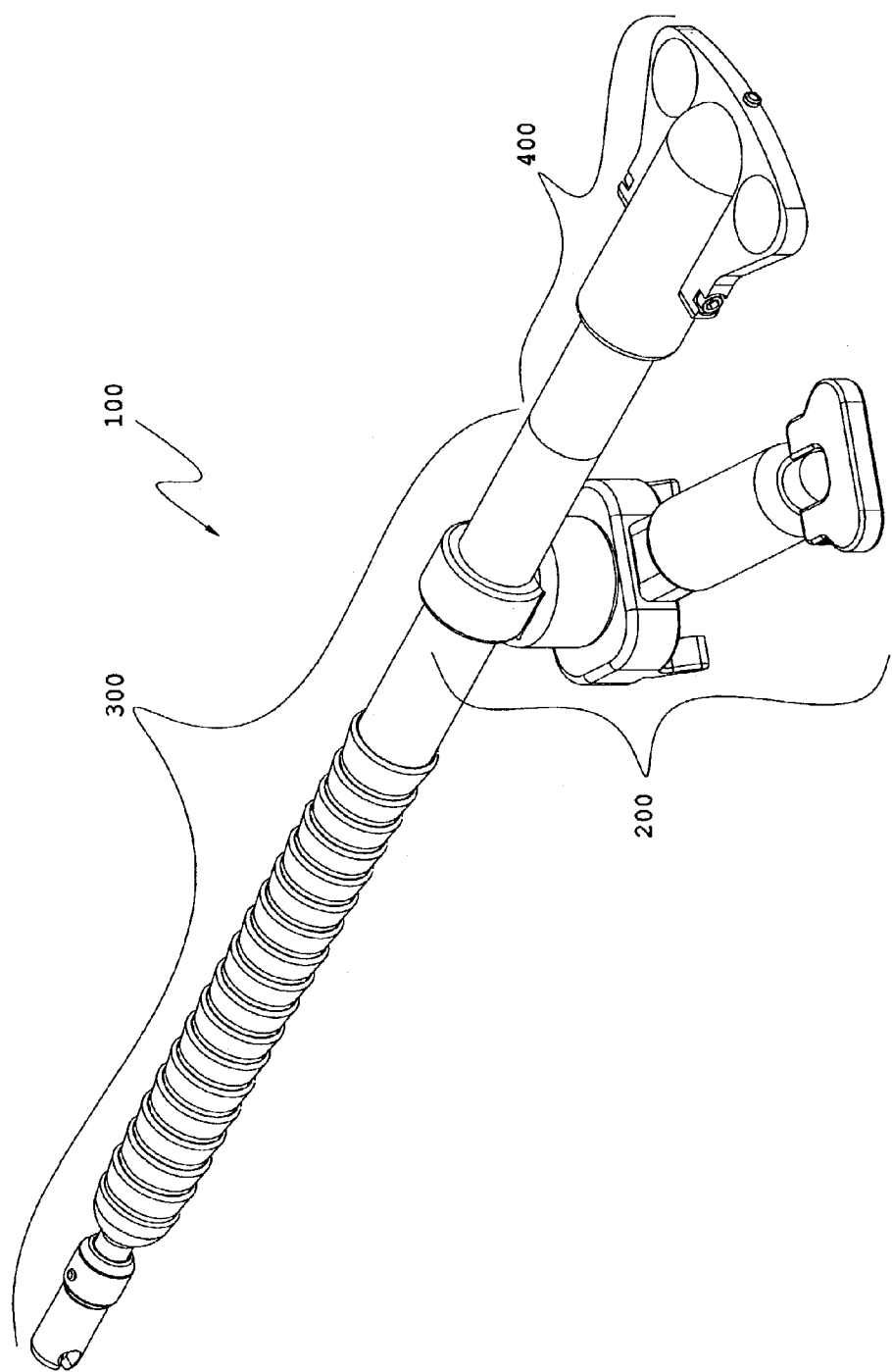
FIG. 1 is a perspective view of a support arm according to the present invention.
Figure 4A:
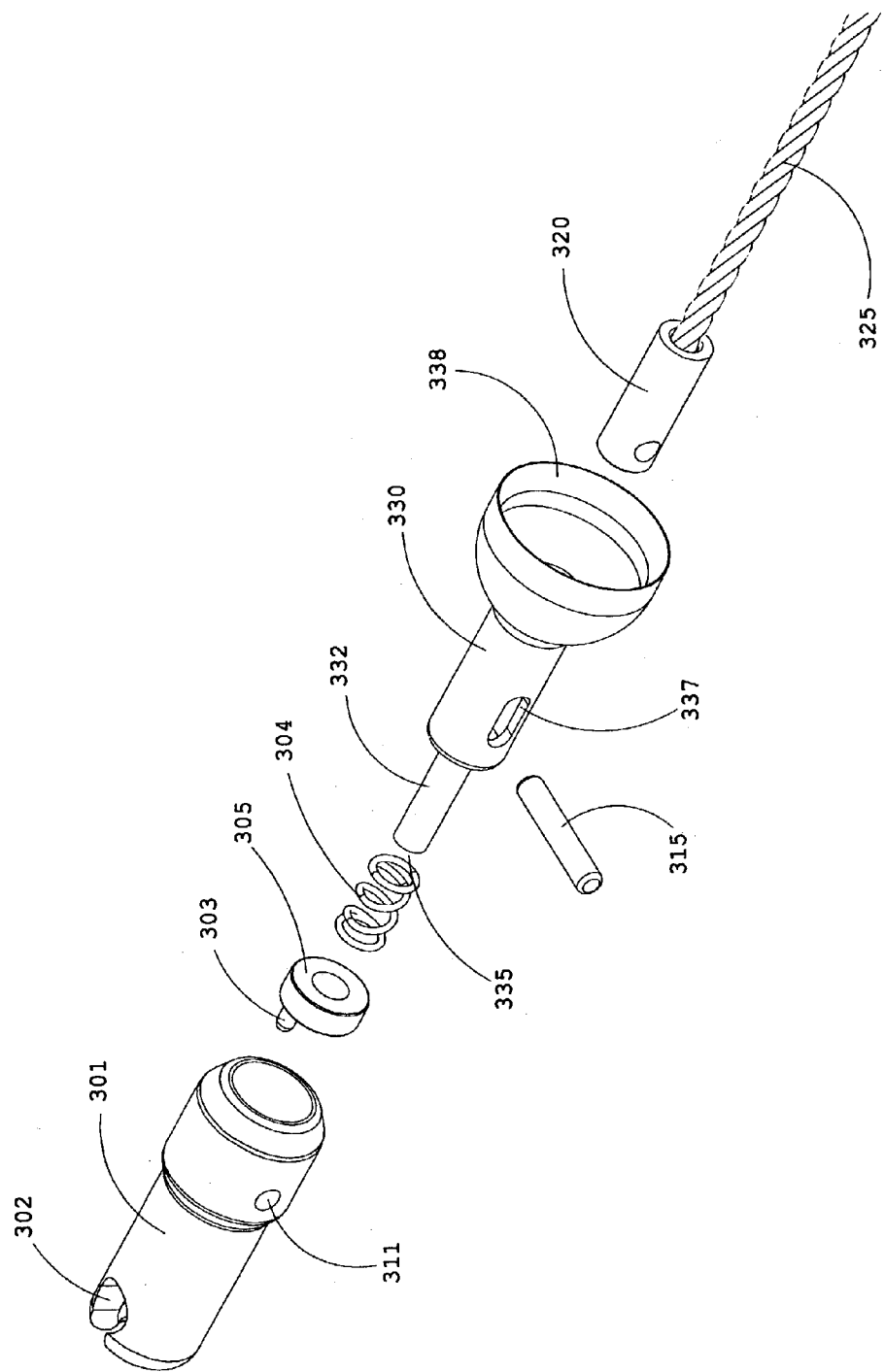
FIG. 4A is an enlarged exploded view of the ball-receiver assembly of FIG. 1.
Figure 4B:
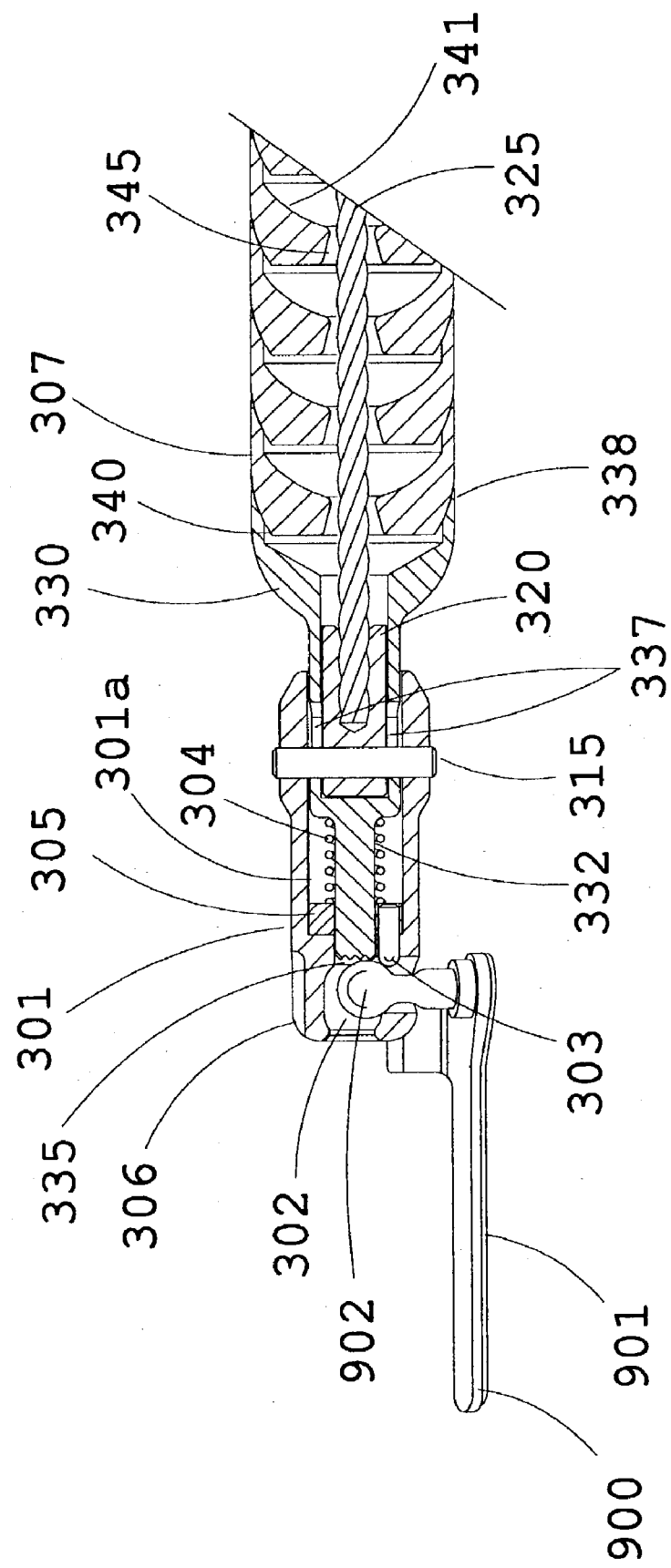
FIG. 4B is an enlarged cross-sectional view of the ball-receiver assembly of FIG. 1 with a typical cardiac stabilizing member snapped into position but not locked.

FIG. 4A is an enlarged exploded view of the ball-receiver assembly 301 of FIG. 1. FIG. 4B is an enlarged cross-sectional view of the ball receiver assembly 301 of FIG. 1 with a typical disposable stainless steel stabilizing cardiac member 900 (having ball fixation pillar 902 and with non-shedding Velcro® high friction cardiac contact surface 901) snapped into loose retention (unlocked position). Referring to FIGS. 4A and 4B, socket housing or receiver 301 has a ball cavity 302 that snap-fit engages the ball feature 902 of the device to be attached. The snap-fit is accomplished by a plunger 305 having a ball-ended pin 303 which is received in a cylindrical cavity 301A in the receiver 301. The plunger 305, including the pin 303, moves axially against the biasing force of spring 304 within cylindrical cavity 301A to allow the attachment to enter the ball cavity 302 and to thereafter hold the ball within the cavity. The receiver 301 is pinned through dowel holes 311 by dowel pin 315, fixing it to a cable end 320, such that the receiver 301 and cable end 320 always move together. The cable end 320 is crimped onto the cable 325. The receiver 301 also has a partial-depth slot 306, for visual reference opposite of the entry to the ball cavity 302. A spring plunger 330 partially resides within the receiver 301 and is movable axially thereof.

Figure 4C:
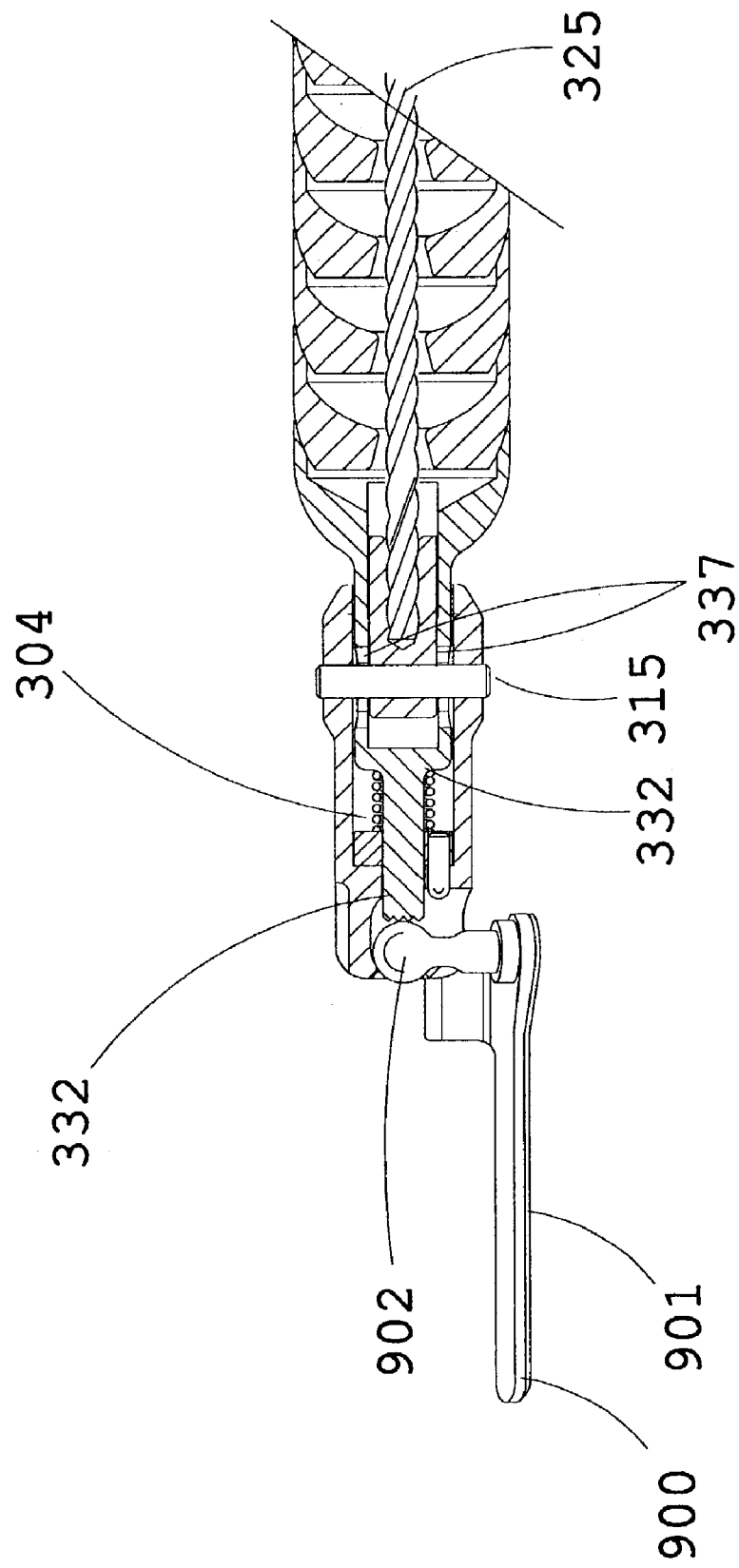
FIG. 4C is an enlarged cross-sectional view of the ball-receiver assembly of FIG. 1 with a typical cardiac stabilizing member locked into position.

The cable end 320 fits axially within a bore of the spring plunger, and is located by dowel pin 315 through axially extending slots 337, in the spring plunger, which allows for axial translation of the cable end 320 relative to the spring plunger 330 but constrains radial rotation. The spring plunger 330 has a snout 332 that protrudes through and internal bore of the ball receiver 301 into a ball cavity 302. The snout may have an end a face 335 having a simple circular recess or the face may be highly textured. Both embodiments ensure secure incidence onto the ball feature of the attachment. Spring plunger 330 is preferably made of a corrosion resistant hardened stainless steel (such as 17/4 PH or 420 or 440 C) suitable heat treated and preferably passivated by electopolishing. In general it is desirable that the spring plunger 330 be harder than the "trailer hitch" stainless steel ball 902 used on the attachment. In use, with tension applied to the cable 325 the receiver 301 is drawn to the right, as shown in FIG. 4C. This causes the snout 332 to extend further into the ball cavity 302, securing the ball therein. On the proximal end, the spring plunger 330 has a concave spherical surface 338 that mates to the convex spherical surface 340 of the first link 307 of a series of identical links.

The links 307 are all identical components, preferably made of a 300 series stainless steel with a convex spherical shoulder 340 of approximately 0.312 inches radius of curvature, but this is not critical and other radii may be used with similar effect. Each link 307 has an axially offset annular concave spherical surface 338 opposite the convex shoulder 340. The surface of the convex shoulder 340 of each link is roughened and hardened to induce a preferential friction relationship against the concave spherical surface 338 of the adjacent link. Alternatively, the concave spherical surface could be roughened and hardened. Roughening is readily accomplished by sand blasting using a suitable grit size. Alternatively spherical surfaces roughening may be by glass beading. A hard surface may be applied to the roughened surface by surface treatment such as the deposition of Titanium Nitride on the roughened surface. It is desirable to have the mating spherical surface smooth and uncoated. The number of links used may be varied depending upon the size of the link used and the overall desired length of the articulating arm. In the preferred embodiment of the invention 12–14 links are used, but the number is not critical. The ultimate link 307A mates with arm-tube transition member 350 (see FIG. 2) which has a convex spherical surface 340 (of the same spherical radius as surface 338 of the links 307) to mesh with concave hemispherical surface 338 of the ultimate link. On its other end transition member 350 has a cylindrical recess 351 to accommodate ramp driver 352, which is interference fit in a counter-sink within cylindrical recess 351. An axial concentric hole 353 through arm-tube transition member 350 allows unimpeded cable movement. Likewise, an axial concentric hole 354 through ramp driver 352 allows unimpeded cable movement. Ramp body spring 356 is a clearance fit on ramp driver 352 and a clearance fit in recess 359 of ramp body 360. The internal diameter of cylindrical recess 351 in arm-tube transition member 350 is such that it is a sliding fit on the outside diameter of ramp body 360. A small hole 355 located in the lower quadrant of ramp driver 352 is to receive the plain end 357a of machine ramp screw 357.

Figure 6:
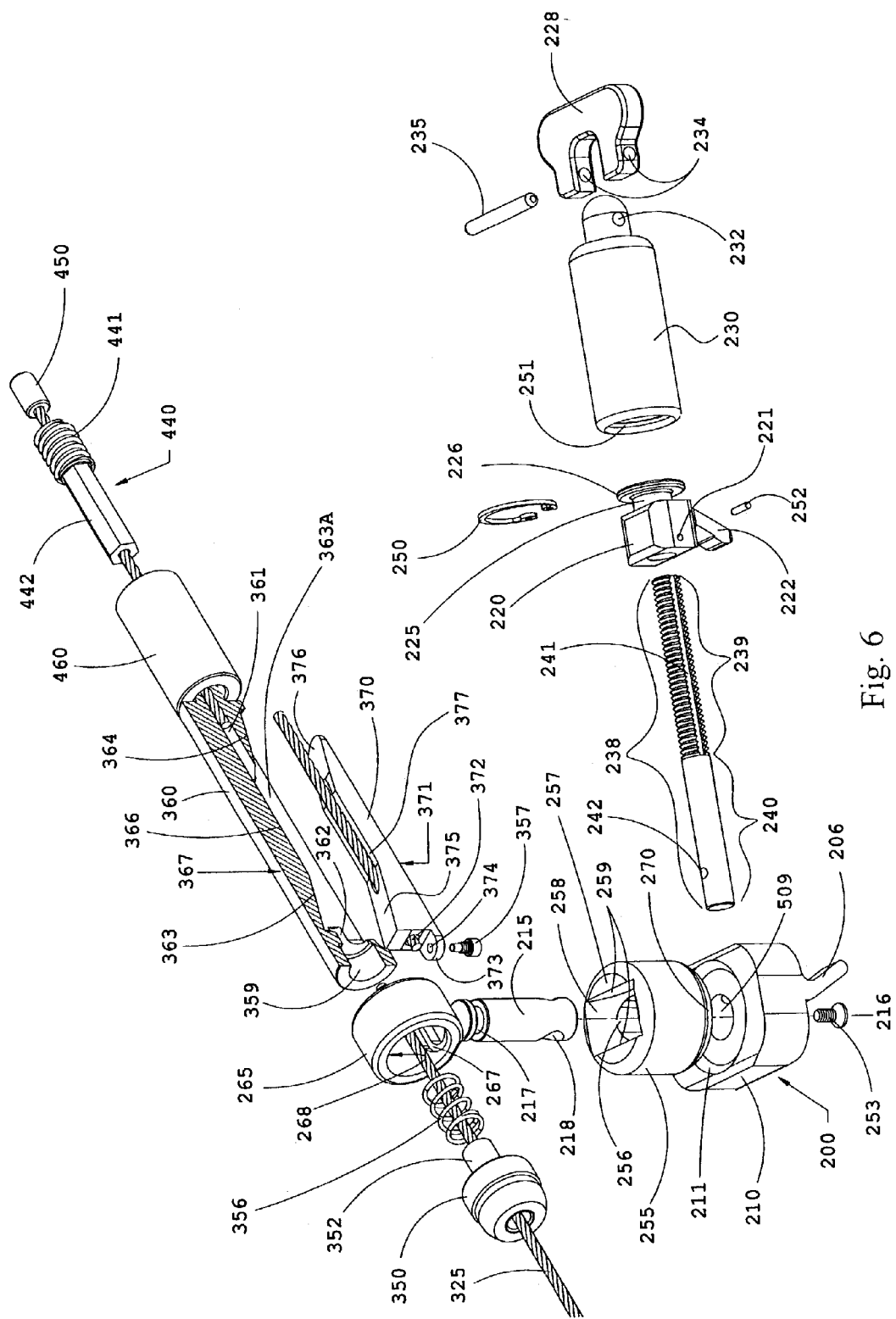
FIG. 6 is an enlarged exploded view of the clamp base and portion of the articulating arm it engages of FIG. 1.

The ramp body 360 (shown in partial cut-away in FIG. 6 and shown in part cross-section for clarity in FIG. 2) has an uppermost surface designated 367, an axial hole 361 for unimpeded cable movement, a cylindrical recess 362 to slidably accommodate ramp driver 352, a second cylindrical recess 359 to accommodate spring 356 and a threaded nipple 368 (See FIG. 2). The ramp body also has a longitudinally machined slot 363A approximately 0.250 inches in width. Ramp body 360 further has a forward machined incline plane 363 and a parallel rearward inclined plane 364 separated by a planar face 366 parallel to a longitudinal axis of the ramp body 360.

The machined ramp 370 has a lower surface 371 and an axial through hole 372 for unimpeded passage of cable 325, and is of such width as to closely slidably fit in the slot 363a in ramp body 360. A small tongue 373 with a threaded hole 374 protrudes from the front of machined ramp 370. Machined ramp 370 has a forward incline plane 375 and a parallel rearward inclined plane 376 separated by a planar face 377 which is parallel to a longitudinal axis of the through hole 372 and lower face 371. Machine ramp 370 moved by the ramp driver 352 by the plain section 357a of screw 357 (See FIG. 3).

When the cable 325 becomes under tension the links 307 are brought into compression. As the cable tension is increased the mating spherical surfaces 340 and 338 are bound into a frictional lock. As the tension in the cable 325 is reduced, the absolute frictional force between the links is also reduced, and the links 307 will again move relative to each other. In use the cable tension can be adjusted so that the links 307 maintain a select position unless moved by the user and then can be locked into place by increasing the cable tension. The links have a clearance 341 cut into the belly to provide clearance for the shoulder 340 as the adjacent links translate with respect to one another. The cable 325 of the system runs through the tapered bore 345 of the links. The tapered bore 345 provides bending relief for the cable 325 between the adjacent links 307.

The ramp body 360, machined ramp 370, slide loop 265, slide cradle 255, pivot 215, and clamp base 205 cooperate to define an axial clamp for the articulated arm as well as a vertical constraint system referenced on the clamp base 200. The slide loop 265 and pivot 215 are tensile elements of this system, and the slide cradle 255, machined ramp 370, and ramp body 360 are compressive elements. At rest (no tension in cable 325), the system is freely movable and unlocked. As tension develops in the cable 325, the arm-tube transition 350 and the ramp driver 352 and hence the inclines 375, 376 of the machined ramp 370, are drawn against and along the ramp body 360 inclines 363, 364.

This effectively lengthens the chord 367 to 371 (the distance from the top of the ramp body 360 to the bottom of the machined ramp 367) in relation to the tension in the cable 325. The complimentary chord from the top flat surface 257 of the slide cradle 255 to the upper inner quadrant 268 of the slide loop is held constant by the anchoring of the slide loop 265 onto the head groove 217 of the clamp base pivot 215 which is locked into the clamp 205 by the clamp shaft 238. A binding compression develops through the stack of the ramp body 360, machined ramp 370, slide cradle 255 and clamp base 205 as the cable 325 is tightened locking the articulating arm assembly from sliding axially through the slide loop 265 and locking the arm/slide loop(265)/slide cradle(255) assembly axially and from rotating around the vertical pivot 215. The ramp driver 352 and arm tube transition 350 are predisposed to move away from the ramp body 360 by the ramp body spring 356, such that the system unlocks when the tension on cable 325 is relieved.

Figure 5:
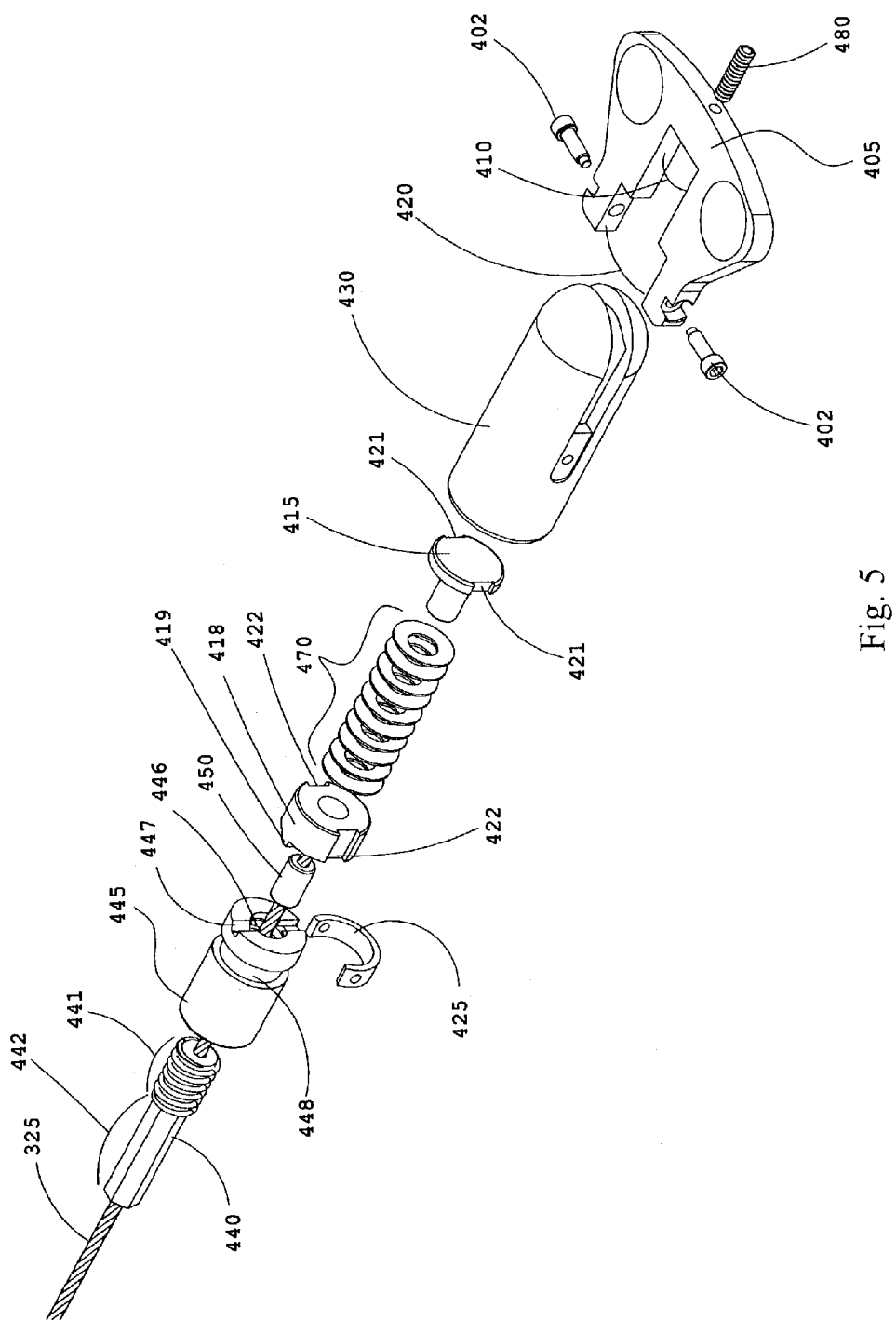
FIG. 5 is an exploded view of the torque-limiting knob system of FIG. 1.

The articulating arm assembly is locked by imparting tension in cable 325, creating the locking binding in the link and ramp body assemblies. This tension is imparted through the torque-limiting knob assembly 400 illustrated in FIGS. 3 and 5. The machined wing 405 has an internal bore 410 having a non-circular cross-section that axially receives a spring base 415 and a knob driver 418 each having complimentary recesses 421, 422 respectively in their outer-diameters (See FIG. 5) which mate with the internal bore 410 to allow for axial movement of these pieces relative to the machine wing 405, but which fixes them radially relative to the machined wing 405. A larger diameter distal position of the internal bore 410 similarly has such a non-circular cross-section 420 to similarly mate with a knob cover 430. With this constraint, the wing 405, knob cover 430, spring base 415 and knob driver 418 always turn together. Also, the wing 405 and an Acme nut 445 are constrained axially, as the wing screws 402 fit into a stress relief c-ring 425 located in annular groove 448 in Acme nut 445. The stress relief c-ring 425 distributes the axial load over about 65% of the circumference of the groove 448, so that not all the load carried by the quadrant of the two wing screws 402. Nut 445 utilizes an Acme thread for minimizing friction forces. However, other thread forms could also be used.

Internal hexagonal spacer 460, which has an outside diameter similar to that of ramp body 360, has a fine pitch internal thread 461 that threadably engages with external fine thread 368 on ramp body 360 to tightly lock internal hexagonal spacer 460 to ramp body 360. The internal hexagonal spacer 460 has an internal hexagonal bore 462 that slideably engages an external hexagonal portion 442 of Acme screw 440.

Acme screw 440 has an externally threaded portion 441 that threadably engages an internally threaded portion 446 of Acme nut 445. As the wing 405 is tightened rotation of the Acme screw is prevented by slidable hexagonal interface 442/462, thus the Acme screw 440 is drawn up into the Acme nut 445. As a result, the cable 325 is tensioned by a thrust to the right exerted on the Boeing button 450 crimped onto the cable 325 being as shown in FIG. 3. This in turn imparts a force of the Acme nut 445 against the internal hexagonal spacer 460 at the end of the ramp body 360, which in turn causes compression of the links 307 through the machine ramp 370, ramp driver 352 and arm/tube transition 350 at the end of the tube assembly. The Acme nut 445 is radially constrained by Acme screw 440 having a hexagonal cross-section 442, which is fit closely into the hexagonal bore 462 of the internal hexagonal spacer 460. The internal hexagonal spacer 460 is fixed tight to the ramp body 360 by mating screw threads 368 and 461.

The knob driver 418 has at least two axially extending radial driver ramps 419 that nest with corresponding axially depressed radial nut ramps 447 in the Acme nut 445. As the torque increases, the knob driver 418 tends to move up off of the Acme nut 445 due to the angle of the ramps. The force of the Belleville springs 470 against the knob driver 418 counters this tendency. When the force of the knob driver 418 moving up the ramps 447 allows enough translation for the knob driver 418 to run all of the way up the ramps 447, it slips out of radial constraint with the Acme nut 445, and the wing knob assembly simply turns, without further tightening the Acme nut 445. The breakaway torque is adjusted by a set screw 480 in the wing 405, which forces the spring base 415 against the Belleville springs 470, increasing the preload in the springs.

Figure 7:
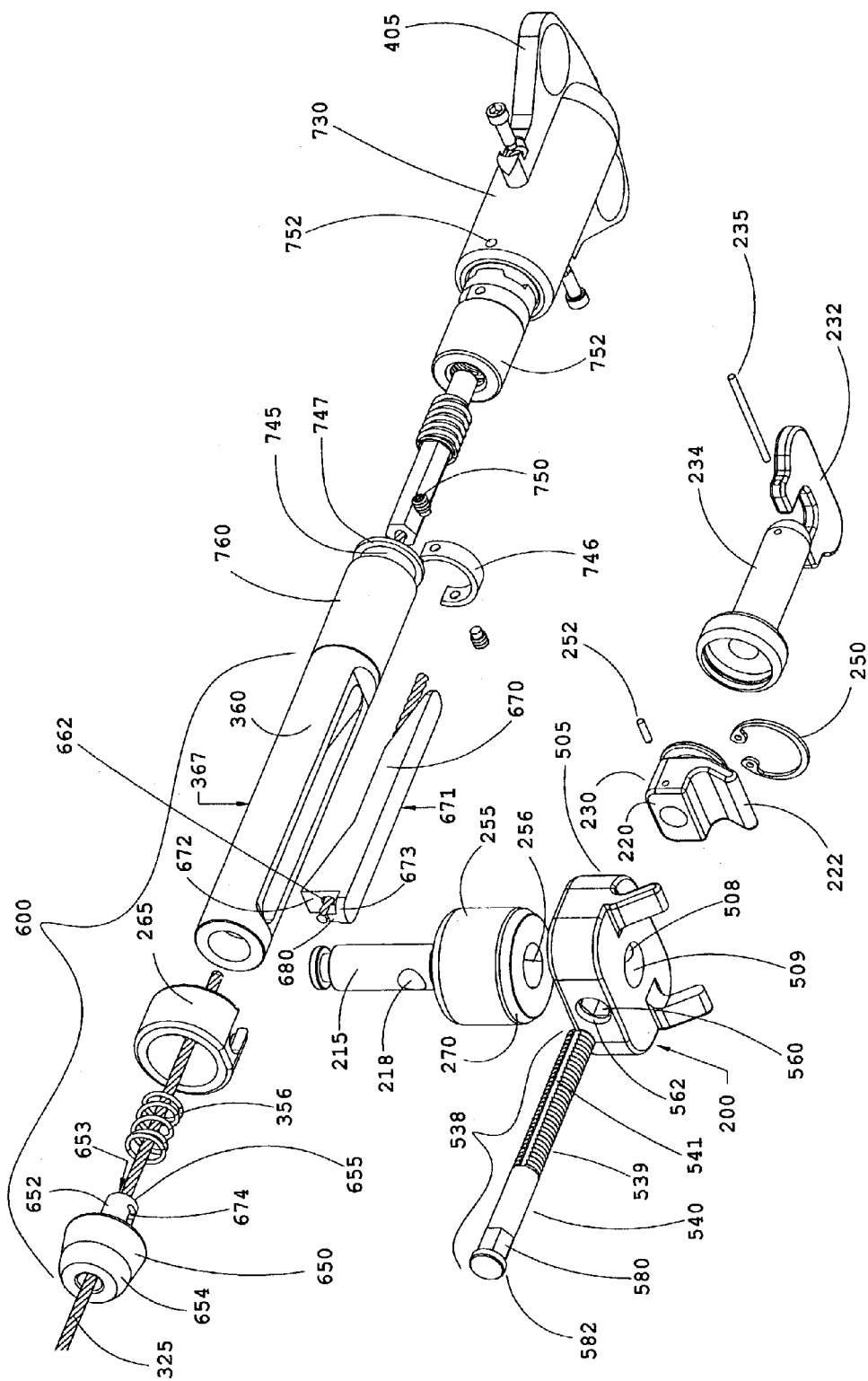
FIG. 7 is an enlarged exploded view of an alternative embodiment of the torque-limiting knob system and of the clamp base assembly of FIG. 1.
Figure 8:
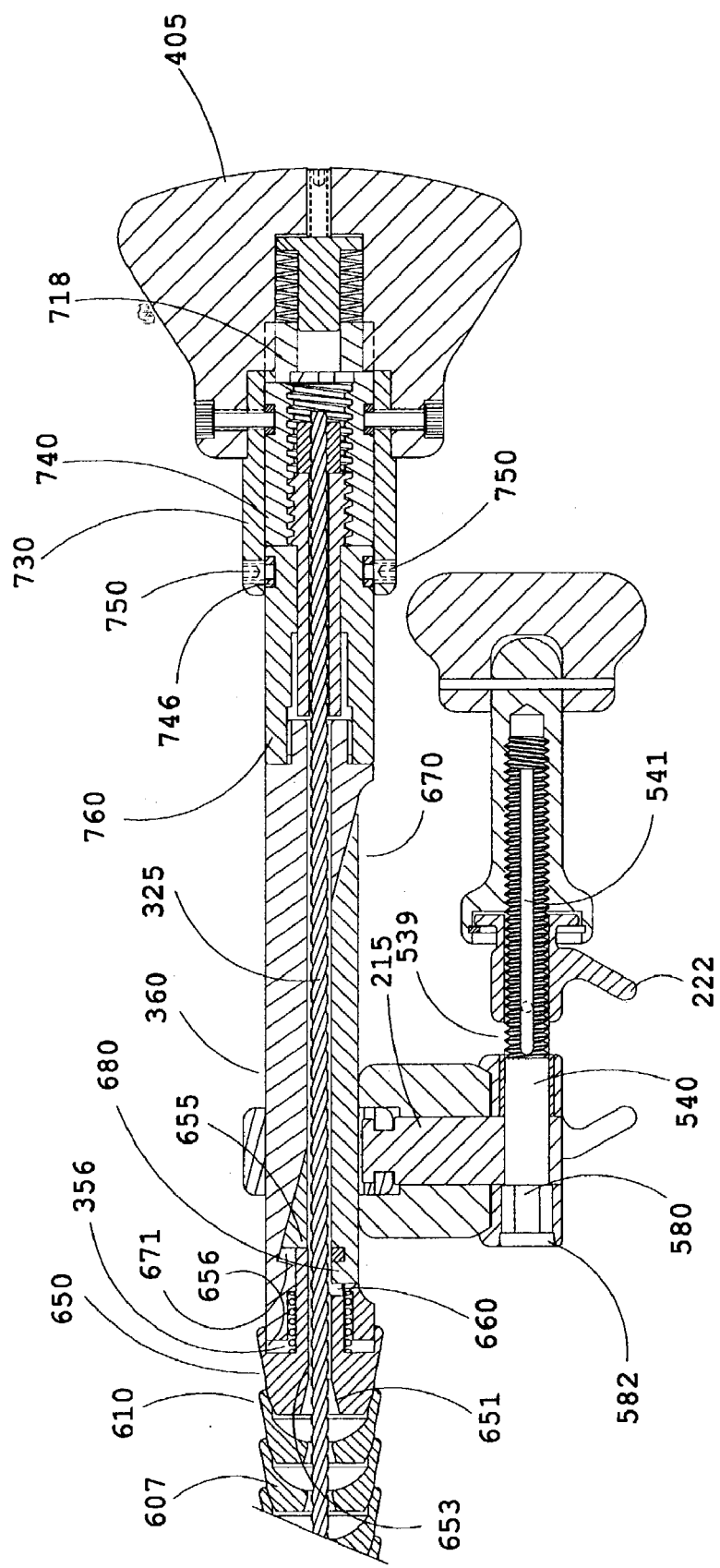
FIG. 8 is a cross-sectional side view of the torque-limiting knob system and of the clamp base assembly of the alternative embodiments of FIG. 7.

An alternative and preferred embodiment to clamp base 200, ramp operating mechanism, articulating links and torque limiting mechanisms are shown in FIG. 7 (an exploded view of the clamp base, ramp and torque limiting assemblies) and FIG. 8 (a mid cross-sectional view of FIG. 7 including several articulating links 607.) Identical elements will have the same reference numbers used above. In FIG. 7 wing 405 is shown rotated through 90° for clarity of illustration. Clamp foundation base 505 has a hexagon recess 560 concentric to opposing cylindrical recess 508, and extending from short cylindrical recess 562 to intersect with vertical central through hole 509. Clamp shaft 538 has a threaded portion 539 with a longitudinal slot 541, a plain portion 540, a hexagonal portion 580 and a short flanged head 582. The threaded portion 539 may conveniently be a ¼ UNC thread, but this is not important and other screw sizes and thread pitches could be used. Hexagonal portions 580 and 560 are oriented such that slot 541 lies in a horizontal plain, thus ensuring that upon assembly when pin 252 in clamp hook 220 is engaged in slot 541 so that opposing finger 222 will lie in a vertical plain. Shaft 538 may conveniently be fixed in position by the application of a heat resistant thread locking compound such as LOC-TITE® 272 to hexagonal portion 580.

With continued reference to FIGS. 7 and 8, in an alternate ramp assembly, machined ramp 670 has tongue 673 and rectangular pillar 680. Arm tube transition member 650 has a cylindrical recess 656 which is a sliding fit on ramp body 360. A through hole 653 in transition member 650 allows for unimpeded passage of cable 325. A tapered recess 651 allows an adjacent articulating link 607 to partially rotate about a spherical convex surface 654 without binding of cable 325. Articulating link 607 has a tapered annular buttress 610 to strengthen the link.

Arm tube transition member 650 has protruding integral ramp driver 652 with a planar end 655 which contacts planar end 672 of machined ramp 670. A through hole 662 in planar face 672 allows for unimpeded cable movement. Protruding integral ramp driver 652 has a Tee shaped slot 674 to receive tongue pillar 680 of machine ramp 670. When the cable comes under tension planar end 655 of integral ramp driver presses against planar end 672 of machine ramp that causes chord distance 367 to 671 to increase, thus effectively widening locking ramp body 360 relative to clamp base foundation 505. The ramp driver 652 and arm tube transition 650 are predisposed to move away from the ramp body 360 by the ramp body spring 356, such that the system unlocks when the tension on cable 325 is relieved.

Internal hexagonal spacer 760 has annular groove 745 with a rearmost face 747 to slideably retain stress relief c-ring 746. The width of the annular groove is wider than that of the c-ring by a predetermined amount of approximately 0.010 inches. Two small set screws 750 threadably engage internal threaded holes 752 of knob cover 730. As wing 405 is backed off, and approximately three complete turns after cable 325 becomes slack, c-ring 746 will contact rearmost portion 747 of annular groove 745, thus preventing further counterclockwise rotation of wing 405 and the removal of the wing and torque locking member during routine use or cleaning. C-ring 746 distributes the axial load over approximately 65% of the circumference of the groove 745 of the hex spacer 760, so that it is not all carried by the quadrant of the two set screws 750. The knob driver 718 mates to the Acme nut 740 with two pairs of opposed radial ramps 747 and 719 in the same manner as discussed above with respect to 419, 447. As the torque increases, the knob driver 718 tends to move up off of the Acme nut 740 due to the angle of the ramps. Acme nut 740 and knob driver 718 may be a hardened yet corrosion resistant stainless such as grade 17/4 PH hardened to 42 Rockville C hardness. Subsequent electropolishing produces further corrosion resistance. These member may also have a vacuum deposited hard surface finish, such as Titanium Nitride to prevent galling.

FIG. 9 shows a plan view of the support arm for cardiac surgery 100 attached to a rack 801 of a sternal retractor 800. A typical cardiac contact member 900 is shown locked in position.

Figure 10:
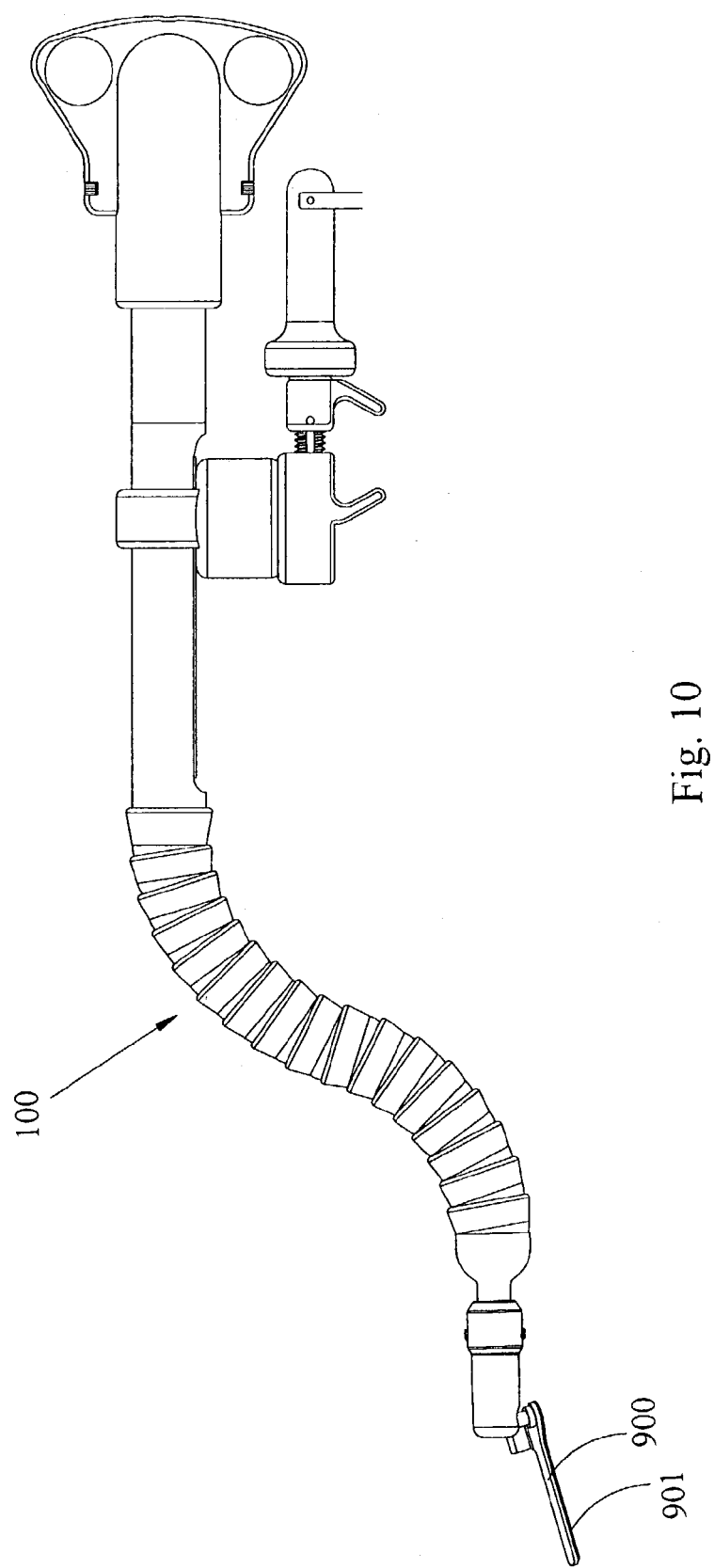
FIG. 10 is a side elevation of the support arm according to the present invention with the arm articulated and advanced. An epicardial stabilizer is shown mounted in the ball retainer.

FIG. 10 illustrates the support arm for cardiac surgery with certain links articulated and a typical cardiac contact means 900 is shown locked in position.

The support arm assembly is preferably manufactured of a corrosion resistant stainless steel, although other suitable metals, such as Titanium could be used. Alternatively, the instrument could be made of a suitable plastic of composite material that has sufficient hardness and durability and that could be sterilized in a steam autoclave or using a Ethylene Oxide gas as a sterilization means.

Figure 11A:
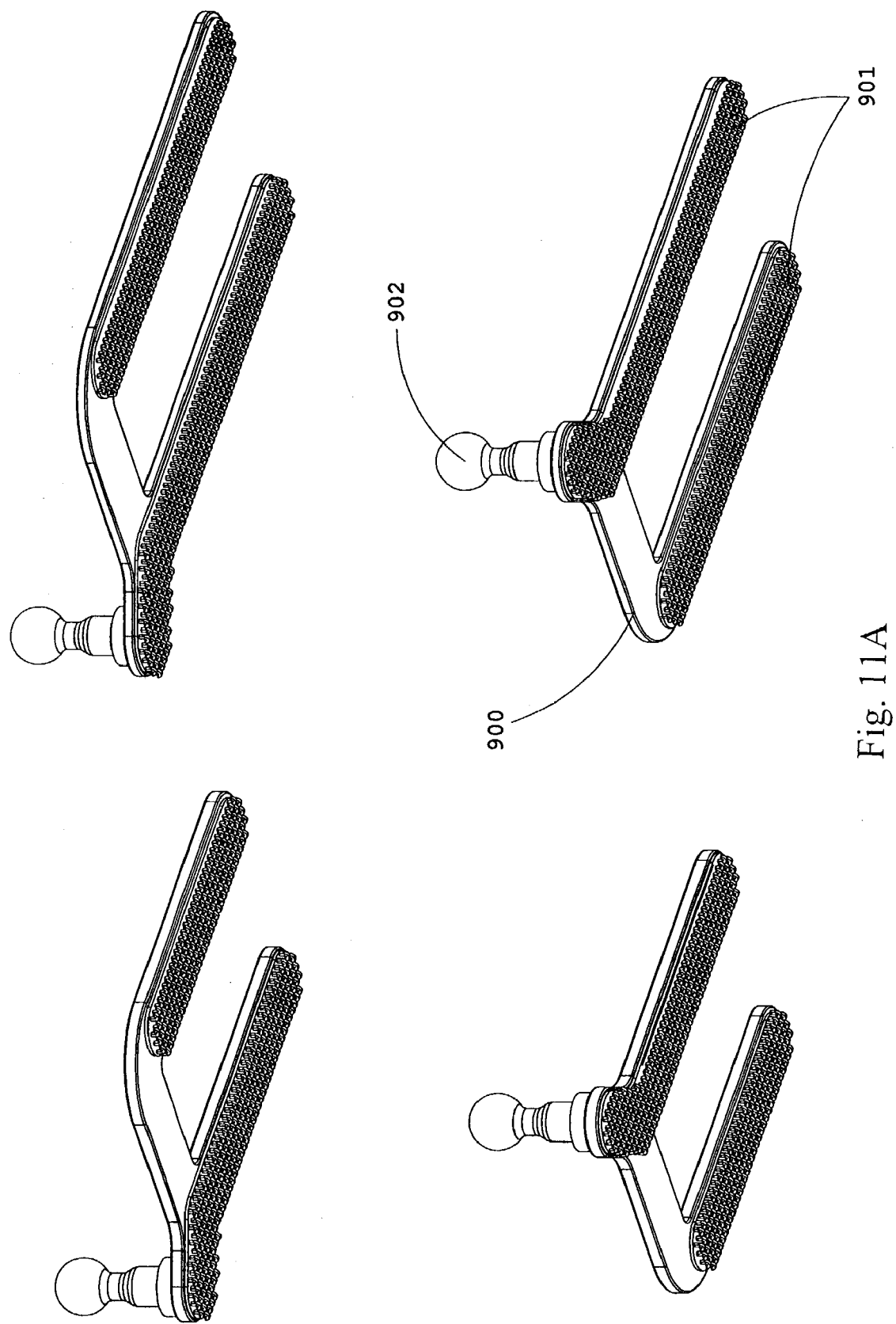
FIGS. 11A–11C are perspective view of representative contact members having varying configurations.
Figure 11B:
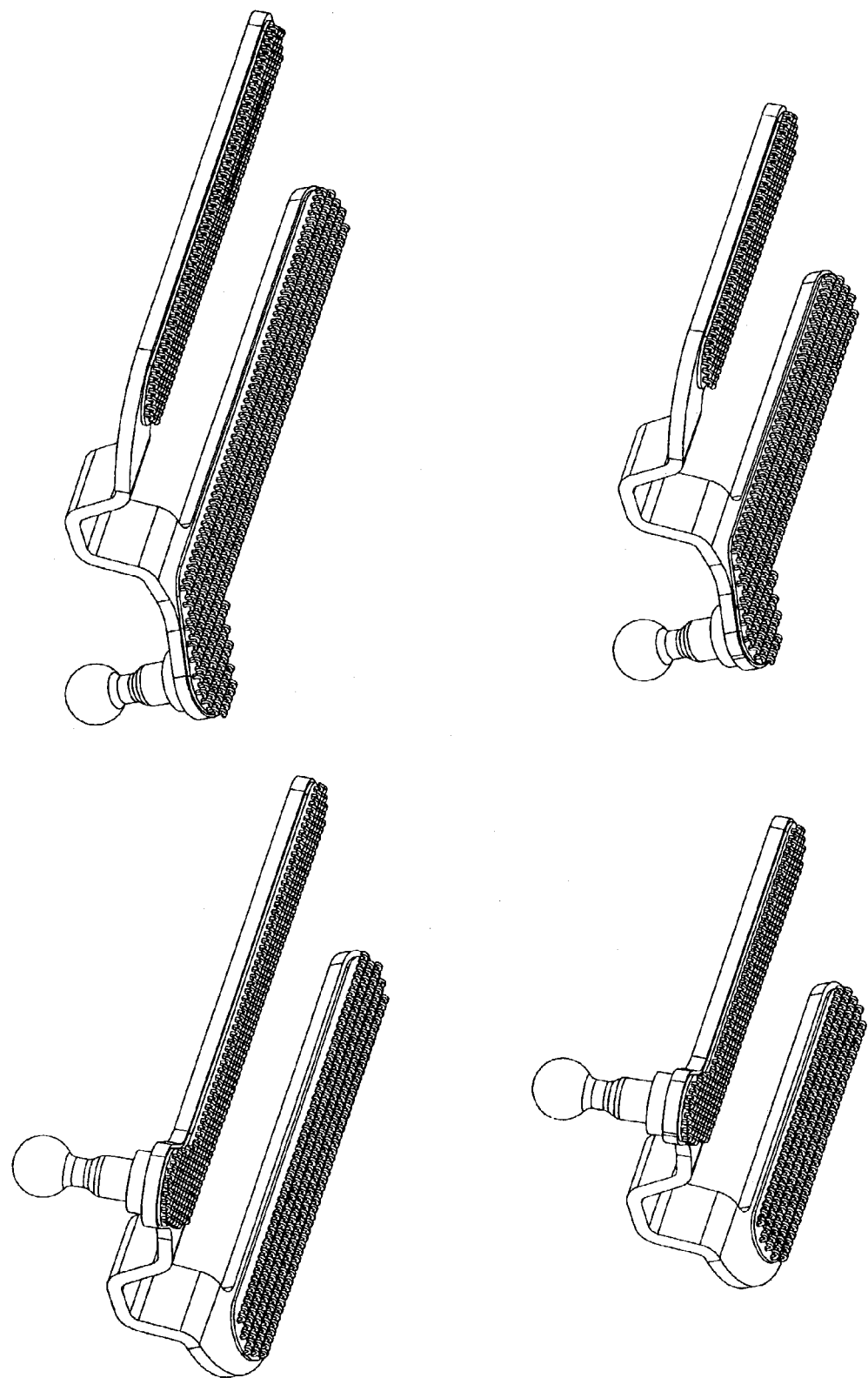
Figure 11C:
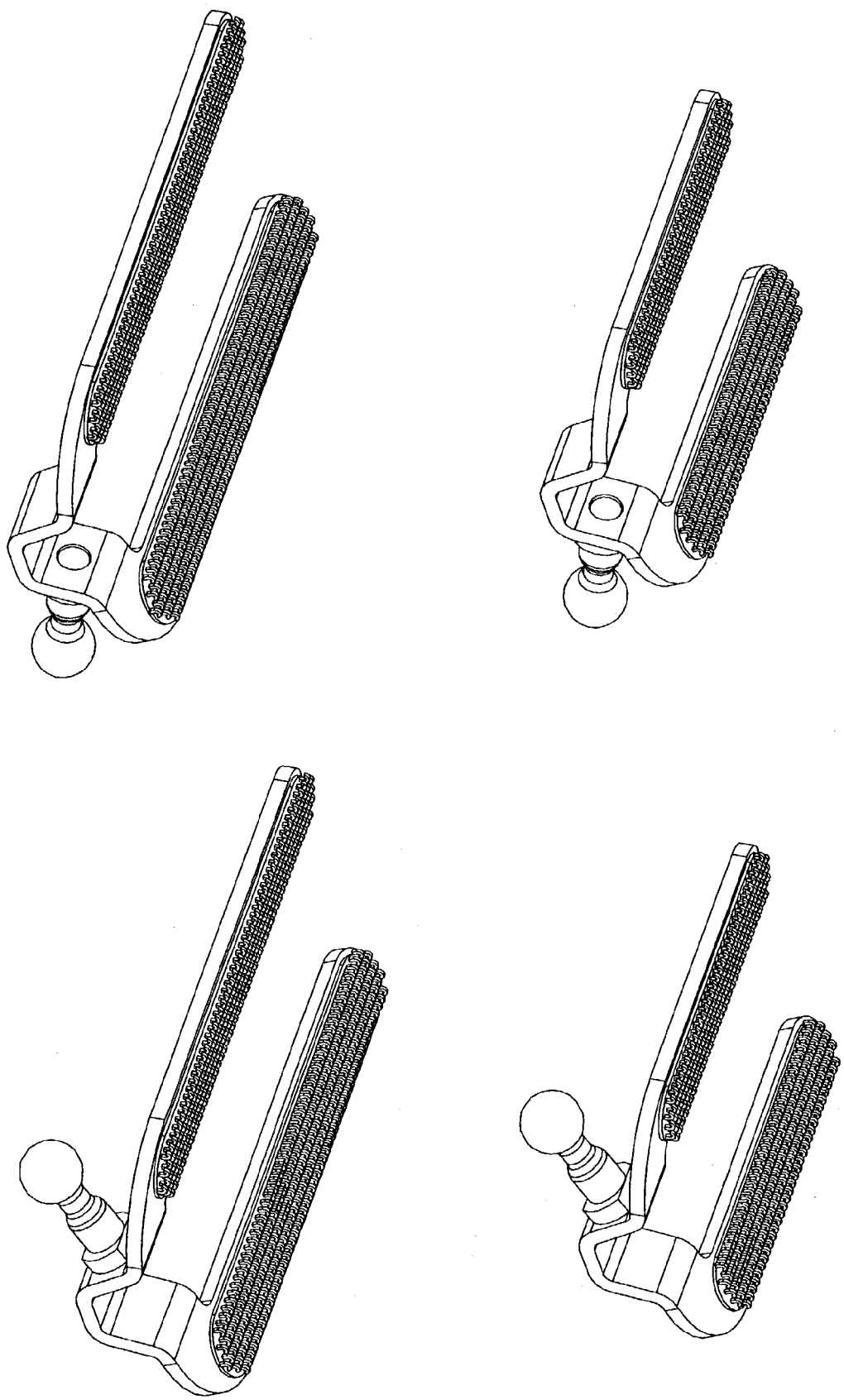

The support arm assembly is useful for a variety of cardiac surgery techniques including coronary artery bypass surgery carried out using cardio-pulmonary bypass and cardiac valve surgery. Such procedures begin with making an incision in the patient's chest, more particularly at the patient's sternum. A sternal retractor 800 is inserted into the incision and opened to provided access to the heart. The support arm assembly 100 is attached to the rack 801 of the sternal retractor 800 as illustrated in FIG. 9. The knob 228 is tightened to bring the fingers 206, 208 and 222 into secure engagement with the rack 801. The knob 400 is maintained loose to allow for adjustment and configuration of the articulated arm 300. The physician then selects one of the interchangeable contact members depicted in FIGS. 11A–11C and inserts the ball into the receiver where it is prevented from falling out by the spring biased finger 303. The surgeon can then apply some tension to the cable 325 turning the wing 405 in a first direction. Sufficient tension is applied to allow for movement of the articulated arm 300 about its various adjustments as discussed above so that the surgeon can bring the contact member into contact with a desired portion of the heart. The articulated arm 300, including the rigid portion of the articulated arm 300, is long enough to provide access to any portion of the patient's heart. Once the surgeon has configured the articulated arm 300 as desired, oriented the contact member as desired, rotated the support arm about the base as desired and axially adjusted the support arm relative to the axial clamp as desired so as to contact the desired portion of the heart, all adjustments of the arm are rigidly fixed to exert and maintain a stabilizing force on the desired portion of the heart simply by turning the wing 405 further in the first direction to fully tension the cable 325. As discussed above, the clutch mechanism prevents over tensioning of the cable so that the physician can concentrate on patient care without concern for damaging the support arm assembly. As should be readily apparent, where the surgical procedure is a coronary artery bypass graft procedure any anastomotic site on the heart may be accessed and exposed using the apparatus. Where the surgical procedure is one being performed on a cardiac valve, the support arm apparatus can be positioned anywhere on the heart as desired by the physician to improve exposure to an atrium, aorta or pulmonary artery as the surgical procedure is performed.

What is claimed is:

1. A support arm assembly for assisting in the performance of cardiac surgery comprising:
   an articulated support arm comprising a plurality of links;
   a cable extending between a distal end and a proximal end of the support arm, the cable being operatively associated with the links of the articulated support arm so that when tensioned the cable compresses the links;
   tensioning means operatively associated with the cable for tensioning the cable; and
   clutch means operatively associated with the tensioning means for preventing application of a tensile force to the cable greater than a select maximum tensile force, wherein the select maximum tensile force is adjustable.

2. The support arm assembly of claim 1 wherein the tensioning means comprises:
   a first end of the cable being fixedly attached to a socket housing;
   a hole in each link receiving the cable;
   a knob having a threaded receptacle, the knob being rotatable relative to the plurality of links; and
   a threaded member that is received in the threaded receptacle and fixed against rotation relative to the links, a second end of the cable being attached to the threaded member, whereby as the knob is rotated in a first direction the threaded member is advanced within the receptacle to tension the cable and as the knob is rotated in a second direction the threaded member is withdrawn from the receptacle to slacken the cable.

3. The support arm assembly of claim 2 wherein the adjustable clutch means comprises:
   at least one radial driver ramp, the driver ramp being fixed against rotation relative to the knob within a knob housing;
   an acme nut received within the knob housing to define the threaded receptacle, the acme nut having an abutting end having a radial nut ramp nesting with the radial driver ramp; and
   a spring compressing the radial driver ramp against the acme nut with the radial driver ramp and the radial nut ramp nested, whereby the radial driver ramp and the radial nut ramp will disengage if a tensile force on the cable exceeds a select amount as the knob is rotated in the first direction.

4. The support arm assembly of claim 1 further comprising:
   a base including means for fixed attachment to a support; and
   an axial clamp extending from the base and axially receiving the articulated support arm, the axial clamp having a locked position preventing axial movement of the support arm relative to the axial clamp and an unlocked position enabling axial movement of the support arm relative to the axial clamp; and
   means operatively associated with the cable for actuating the axial clamp to the locked position as the cable is tensioned.

5. The support arm assembly of claim 4 wherein the base further comprises:
   a pivotal connection between the base and the axial clamp enabling rotation of the axial clamp relative to the base; and
   means operatively associated with the cable for fixing the pivotal connection with the axial clamp in a select rotated position relative to the base as the cable is tensioned.

6. The support arm assembly of claim 1 further comprising:
   a base including means for fixed attachment to a support;
   a pivot between the base and the support arm enabling pivoted radial positioning of the support arm relative to the base; and
   means operatively associated with the cable for fixing the support arm in a select pivoted radial position relative to the base as the cable is tensioned.

7. A support arm assembly for assisting in the performance of cardiac surgery comprising:
   a base including means for fixed attachment to a support;
   an articulated support arm having a select orientation; and
   an axial clamp extending from the base and axially receiving the articulated support arm, the axial clamp having a locked position preventing axial movement of the support arm relative to the axial clamp and an unlocked position enabling axial movement of the support arm relative to the axial clamp, whereby actuation of a single control fixes the orientation of the articulated support arm and substantially simultaneously fixes the axial clamp in a locked position.

8. The articulated support arm assembly of claim 7 further comprising:
   means for connection between a contact member and a distal end of the articulated support arm to enable the contact member to assume a select orientation relative to the articulated support arm and actuation of the single control locks the select orientation of the contact member relative to the articulated support arm.

9. The support arm assembly of claim 8 further comprising:
   a pivotal connection between the base and the axial clamp enabling rotation of the axial clamp relative to the base; and
   a fixing means operatively associated with the pivotal connection for fixing the axial clamp in a select rotated position relative to the base by actuation of the single control.

10. The support arm assembly of claim 9 wherein the fixing means comprises a cable extending between the means for connection and a proximal end of the articulated arm, the cable being operatively associated with the articulated support arm, the clamp and the means for connection so that as the cable is tensioned the support arm is fixed in a select configuration, the axial clamp is fixed in the locked position and the means for connection is fixed with a select orientation relative to the support arm and the single control comprises a knob rotatably attached to the proximal end of the support arm, the cable being operatively associated with the knob, and the knob being configured so that as it is rotated in a first direction any tension in the cable is increased and as it is rotated in a second direction any tension in the cable is decreased.

11. The support arm assembly of claim 8 wherein the support arm comprises a proximal rigid portion and a distal articulated portion, the proximal rigid portion being axially received by the axial clamp.

12. A support arm assembly for assisting in the performance of cardiac surgery comprising:
   a base including means for fixed attachment to a support;
   an articulated support arm comprising a plurality of links;
   a cable extending between a distal end and a proximal end of articulated the support arm, the cable being operatively associated with the links of the articulated support arm so that when tensioned the cable compresses the links;

tensioning means operatively associated with the cable for tensioning the cable; thereby fixing the orientation of the support arm;

a contact member for contacting the surface of the heart operatively associated with a distal end of the support arm; and a pivot between the base and the support arm enabling pivoted radial positioning of the support arm relative to the base, whereby actuation of a single control fixes the orientation of the articulated support arm and substantially simultaneously fixes the pivot in a locked position.

* * * * *